(12) United States Patent
Kitagawa et al.

(10) Patent No.: US 10,398,639 B2
(45) Date of Patent: Sep. 3, 2019

(54) SKIN ADHESIVE SHEET, AND SHEET-LIKE EXTERNAL PREPARATION FOR SKIN

(71) Applicant: TORAY INDUSTRIES, INC., Tokyo (JP)

(72) Inventors: Rumiko Kitagawa, Otsu (JP); Masataka Nakamura, Otsu (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 15/574,653

(22) PCT Filed: May 27, 2015

(86) PCT No.: PCT/JP2015/065250
§ 371 (c)(1),
(2) Date: Nov. 16, 2017

(87) PCT Pub. No.: WO2016/189697
PCT Pub. Date: Dec. 1, 2016

(65) Prior Publication Data
US 2018/0125775 A1 May 10, 2018

(51) Int. Cl.
| | | |
|---|---|---|
| *A61K 8/91* | (2006.01) | |
| *A61Q 19/00* | (2006.01) | |
| *A61K 8/895* | (2006.01) | |
| *A61K 47/34* | (2017.01) | |
| *A61K 9/70* | (2006.01) | |
| *A61L 15/58* | (2006.01) | |
| *A61K 8/02* | (2006.01) | |
| *A61K 8/891* | (2006.01) | |
| *A61K 8/897* | (2006.01) | |

(52) U.S. Cl.
CPC .............. *A61K 8/91* (2013.01); *A61K 8/0208* (2013.01); *A61K 8/0216* (2013.01); *A61K 8/891* (2013.01); *A61K 8/895* (2013.01); *A61K 8/897* (2013.01); *A61K 9/70* (2013.01); *A61K 47/34* (2013.01); *A61L 15/58* (2013.01); *A61Q 19/00* (2013.01); *A61Q 19/007* (2013.01); *A61K 2800/87* (2013.01)

(58) Field of Classification Search
CPC . A61K 8/81; A61K 8/895; A61K 8/02; A61K 8/0216; A61K 8/91; A61K 9/70; A61K 47/34; A61K 2800/87; A61Q 19/00; A61Q 19/007; A61L 15/58
See application file for complete search history.

(56) References Cited

U.S. PATENT DOCUMENTS

| | | | |
|---|---|---|---|
| 4,136,250 A | 1/1979 | Mueller et al. | |
| 4,189,546 A | 2/1980 | Deichert et al. | |
| 4,972,037 A | 11/1990 | Garbe et al. | |
| 5,229,435 A | 7/1993 | Sakai et al. | |
| 8,124,689 B2 | 2/2012 | Loubert et al. | |
| 2014/0198295 A1* | 7/2014 | Fujisawa | A61L 27/34 351/159.33 |

FOREIGN PATENT DOCUMENTS

| | | |
|---|---|---|
| EP | 2745853 A1 | 6/2014 |
| JP | 5422487 A | 2/1979 |
| JP | 02262511 A | 10/1990 |
| JP | 0376713 A | 4/1991 |
| JP | 07508060 A | 9/1995 |
| JP | 09206369 A | 8/1997 |
| JP | 11228340 A | 8/1999 |
| JP | 2007020597 A | 2/2007 |
| JP | 2009540052 A | 11/2009 |
| JP | 2013172764 A | 9/2013 |

OTHER PUBLICATIONS

Rumiko et al., (JP 2013172764 A, 2013, using Eng. Translation) 2013.*
International Search Report and Written Opinion for International Application No. PCT/JP2015/065250, dated Aug. 25, 2015—7 Pages.

* cited by examiner

*Primary Examiner* — Blessing M Fubara
(74) *Attorney, Agent, or Firm* — RatnerPrestia

(57) ABSTRACT

A skin adhesive sheet is disclosed which is good in tackiness to the skin surface, does not easily dry even when used for a long time, can maintain flexibility, and is small in the shape variation. The skin adhesive sheet includes a copolymer containing the following components A and C as polymerization components, and having a water content less than 10% by mass: component A: a polysiloxane macromonomer having a plurality of polymerizable functional groups per molecule, and having a number average molecular weight of 6,000 or more; and component C: a polymerizable monomer having an alkyl group and having no fluoroalkyl group.

11 Claims, No Drawings

SKIN ADHESIVE SHEET, AND SHEET-LIKE EXTERNAL PREPARATION FOR SKIN

CROSS REFERENCE TO RELATED APPLICATIONS

This is the U.S. National Phase application of PCT/JP2015/065250, filed May 27, 2015, the disclosure of this application being incorporated herein by reference in its entirety for all purposes.

TECHNICAL FIELD OF THE INVENTION

The present invention relates to a highly biocompatible skin adhesive sheet used in application to the skin, and a sheet-like external preparation for skin including the skin adhesive sheet and a drug solution held on the surface of the skin adhesive sheet.

BACKGROUND OF THE INVENTION

In recent years, sheet-like external preparations for skin used in application to the skin are known in various fields such as medical materials and cosmetics. These sheet-like external preparations are mainly prepared by impregnating a sheet base material such as a nonwoven fabric or paper with a component effective against the skin, such as a drug solution or a beauty essence, and are used in application to the skin.

Such generally used sheet-like external preparations prepared by impregnating a 100% cotton nonwoven fabric or 100% rayon nonwoven fabric with a drug solution or a beauty essence are effective in that they have high oxygen permeability. However, they have a problem of falling off during use because they have low adhesion to the skin. Furthermore, since such sheet-like external preparations have high water vapor permeability, they have a problem that the drug solution or the beauty essence evaporates from the nonwoven fabric before sufficiently permeating into the skin, and the sheet-like external preparations lack the sustainability of efficacy.

As a sheet-like external preparation for skin improved in adhesion to the skin, a gel sheet containing a polyacrylic acid and/or a polyacrylic acid salt, a polyhydric alcohol, water, and an external crosslinking agent has been proposed (Patent Document 1).

PATENT DOCUMENT

Patent Document 1: Japanese Patent Laid-open Publication No. 11-228340

SUMMARY OF THE INVENTION

However, the gel sheet described in Patent Document 1 does not solve the problem of lack of sustainability of efficacy since it contains a water-containing gel and is not sufficiently suppressed in evaporation of the drug solution or the like.

The present invention has been made in view of the above-mentioned problems, and an object of the present invention is to provide a skin adhesive sheet which is good in adhesion to the skin surface, does not easily dry even when used for a long time, can maintain flexibility, and is small in the shape variation.

In order to achieve the above-mentioned object, one aspect of the present invention provides a skin adhesive sheet including a copolymer containing the following components A and C as polymerization components, and having a water content less than 10% by mass:

component A: a polysiloxane macromonomer having a plurality of polymerizable functional groups per molecule, and having a number average molecular weight of 6,000 or more; and component C: a polymerizable monomer having an alkyl group and having no fluoroalkyl group.

According to the present invention, it is possible to provide a skin adhesive sheet which is good in tackiness to the skin surface, has high oxygen permeability, does not easily dry even when used for a long time, can maintain flexibility, and is small in the shape variation.

DETAILED DESCRIPTION OF EMBODIMENTS OF THE INVENTION

The component A is a polysiloxane macromonomer having a plurality of polymerizable functional groups per molecule, and having a number average molecular weight of 6,000 or more. The number of polymerizable functional groups of the component A is not particularly limited as long as it is 2 or more per molecule. However, the number is preferably 2 per molecule from the viewpoint of easily obtaining a more flexible (low elastic modulus) skin adhesive sheet. It is particularly preferable that the component A have a structure in which polymerizable functional groups are positioned at both ends of the molecular chain.

The polymerizable functional group of the component A is preferably a radical polymerizable functional group, and is more preferably a radical polymerizable functional group having a carbon-carbon double bond. Examples of preferable polymerizable functional groups include a vinyl group, an allyl group, a (meth)acryloyl group, an α-alkoxymethylacryloyl group, a maleic acid residue, a fumaric acid residue, an itaconic acid residue, a crotonic acid residue, an isocrotonic acid residue, and a citraconic acid residue. Among these polymerizable functional groups, a (meth)acryloyl group is most preferable because it has high polymerizability. As used herein, the term "(meth)acryloyl" represents both methacryloyl and acryloyl, and the same shall apply to terms such as "(meth)acrylic" and "(meth)acrylate". In addition, a macromonomer and a monomer having a (meth)acryloyl group as a polymerizable functional group are referred to as a "(meth)acrylic macromonomer" and a "(meth)acrylic monomer", respectively.

When the number average molecular weight of the polysiloxane macromonomer of the component A is 6,000 or more, an adhesive sheet that is flexible and excellent in mechanical properties such as folding resistance can be obtained. If the number average molecular weight of the component A is too small, mechanical properties such as folding resistance tend to deteriorate. Therefore, the number average molecular weight of the component A is preferably 8,000 or more, more preferably 9,000 or more, still more preferably 10,000 or more. If the number average molecular weight of the component A is too large, flexibility and transparency tend to deteriorate. Therefore, the number average molecular weight of the component A is preferably 100,000 or less, more preferably 70,000 or less, still more preferably 50,000 or less.

In the present invention, the number average molecular weight of the component A is the polystyrene-equivalent number average molecular weight as measured by a gel permeation chromatographic method (GPC method) using chloroform as a solvent. The mass average molecular weight and dispersion degree (a value obtained by dividing the mass average molecular weight by the number average molecular weight) are also measured by a similar method.

The component A is preferably a macromonomer having the structure of the following formula (A1):

[Chemical Formula 1]

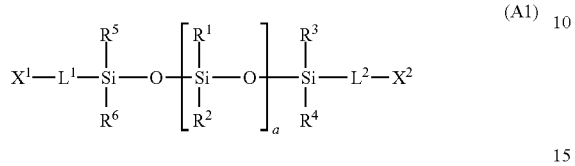

wherein $X^1$ and $X^2$ each independently represent a polymerizable functional group; $R^1$ to $R^6$ each independently represent a substituent selected from hydrogen, an alkyl group having 1 to 20 carbon atoms, a phenyl group, and a fluoroalkyl group having 1 to 20 carbon atoms; $L^1$ and $L^2$ each independently represent a divalent group; a is number of repetitions of siloxane units, and represents an integer of 1 to 1500; and structures of the siloxane units may be the same or different.

The polymerizable functional group represented by $X^1$ or $X^2$ is preferably a radical polymerizable functional group, and is preferably a radical polymerizable functional group having a carbon-carbon double bond. Examples of preferable polymerizable functional groups include a vinyl group, an allyl group, a (meth)acryloyl group, an α-alkoxymethylacryloyl group, a maleic acid residue, a fumaric acid residue, an itaconic acid residue, a crotonic acid residue, an isocrotonic acid residue, and a citraconic acid residue. Among these polymerizable functional groups, a (meth)acryloyl group is most preferable because it has high polymerizability. That is, the component A is most preferably a (meth)acrylic macromonomer.

Suitable specific examples of $R^1$ to $R^6$ include hydrogen; alkyl groups having 1 to 20 carbon atoms, such as a methyl group, an ethyl group, a propyl group, an isopropyl group, a butyl group, a t-butyl group, a decyl group, a dodecyl group, and an octadecyl group; a phenyl group; and fluoroalkyl groups having 1 to 20 carbon atoms, such as a trifluoromethyl group, a trifluoroethyl group, a trifluoropropyl group, a tetrafluoropropyl group, a hexafluoroisopropyl group, a pentafluorobutyl group, a heptafluoropentyl group, a nonafluorohexyl group, a hexafluorobutyl group, a heptafluorobutyl group, an octafluoropentyl group, a nonafluoropentyl group, a dodecafluoroheptyl group, a tridecafluoroheptyl group, a dodecafluorooctyl group, a tridecafluorooctyl group, a hexadecafluorodecyl group, a heptadecafluorodecyl group, a tetrafluoropropyl group, a pentafluoropropyl group, a tetradecafluorooctyl group, a pentadecafluorooctyl group, an octadecafluorodecyl group, and a nonadecafluorodecyl group. Among these groups, hydrogen and a methyl group are more preferable, and a methyl group is most preferable from the viewpoint of imparting satisfactory mechanical properties and high oxygen permeability to the skin adhesive sheet. Therefore, the polysiloxane macromonomer of the component A is most preferably a polydimethylsiloxane macromonomer.

$L^1$ and $L^2$ each independently represent a divalent group, preferably a divalent group having 1 to 20 carbon atoms. Among these groups, groups represented by the following formulas (LE1) to (LE12) are preferable because the compound of the formula (A1) is easily obtained with high purity. Among these, $L^1$ and $L^2$ are more preferably groups represented by the following formulas (LE1), (LE3), (LE9), and (LE11), still more preferably groups represented by the following formulas (LE1) and (LE3), most preferably a group represented by the following formula (LE1). In the following formulas (LE1) to (LE12), the left side is drawn as an end which is bonded to the polymerizable functional group $X^1$ or $X^2$, while the right side is drawn as an end which is bonded to a silicon atom.

[Chemical Formula 2]

  (LE1)

  (LE2)

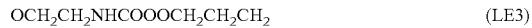  (LE3)

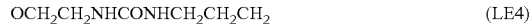  (LE4)

  (LE5)

  (LE6)

  (LE7)

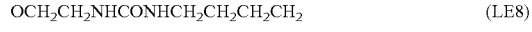  (LE8)

  (LE9)

  (LE10)

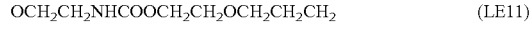  (LE11)

OCH$_2$CH$_2$NHCONHCH$_2$CH$_2$OCH$_2$CH$_2$CH$_2$  (LE12)

In the formula (A1), a is number of repetitions of siloxane units, and represents an integer of 1 to 1500. a is preferably 80 or more, more preferably 100 or more, still more preferably 100 to 1400, even more preferably 120 to 950, yet more preferably 130 to 700.

When the skin adhesive sheet of the present invention is used in, for example, a wound site, it is preferable that the skin adhesive sheet be transparent to the extent that the sheet has no turbidity when visually observed. From the viewpoint of transparency, the dispersion degree (a value obtained by dividing the mass average molecular weight by the number average molecular weight) of the component A is preferably 6 or less, more preferably 3 or less, still more preferably 2 or less, most preferably 1.5 or less. When the component A has a small dispersion degree, the compatibility of the component A with other components is improved, and the transparency of the obtained copolymer is improved. There are also advantages such as reduction of impurities contained in the copolymer, and reduction of the ratio of shrinkage associated with molding of the skin adhesive sheet.

The copolymer of the present invention preferably contains 50 parts by mass or more of the component A based on 100 parts by mass in total of polymerization components of the copolymer. The content of the component A is preferably 50 to 99 parts by mass, and is more preferably 55 to 90 parts by mass, still more preferably 60 to 80 parts by mass, most preferably 65 to 75 parts by mass from the viewpoint of achieving both the oxygen permeability and moderate flexibility.

The component A of the present invention may be used alone, or two or more kinds may be used in combination.

The copolymer constituting the skin adhesive sheet of the present invention may further contain, as a component B, a polymerizable monomer having a fluoroalkyl group as a polymerization component.

When the copolymer contains the component B as a polymerization component, it is possible to impart water and oil repellency to the adhesive sheet due to a decrease in the critical surface tension caused by the fluoroalkyl group of the component B, and the component B exerts an effect of suppressing the contamination of the adhesive sheet surface due to components such as proteins and lipids in a biological fluid. The copolymerization of the component B also has an effect that it is possible to obtain an adhesive sheet that is flexible and excellent in mechanical properties such as folding resistance. Herein, the polymerizable monomer means a monomer having a polymerizable functional group and having a number average molecular weight less than 5,000.

The component B may have a plurality of polymerizable functional groups per molecule, but one having only one polymerizable functional group per molecule (monofunctional polymerizable monomer) is preferable. When the component B is a monofunctional polymerizable monomer, the crosslinking density decreases, the degree of freedom of the copolymer increases, and a moderately flexible skin adhesive sheet having low elastic modulus can be realized.

The upper limit of the number average molecular weight of the component B is preferably less than 1,000, more preferably less than 500, still more preferably less than 300. The lower limit is preferably 90 or more, more preferably 100 or more, still more preferably 130 or more.

Suitable specific examples of the fluoroalkyl group of the component B include fluoroalkyl groups having 1 to 20 carbon atoms, such as a trifluoromethyl group, a trifluoroethyl group, a trifluoropropyl group, a tetrafluoropropyl group, a hexafluoroisopropyl group, a pentafluorobutyl group, a heptafluoropentyl group, a nonafluorohexyl group, a hexafluorobutyl group, a heptafluorobutyl group, an octafluoropentyl group, a nonafluoropentyl group, a dodecafluoroheptyl group, a tridecafluoroheptyl group, a dodecafluorooctyl group, a tridecafluorooctyl group, a hexadecafluorodecyl group, a heptadecafluorodecyl group, a tetrafluoropropyl group, a pentafluoropropyl group, a tetradecafluorooctyl group, a pentadecafluorooctyl group, an octadecafluorodecyl group, and a nonadecafluorodecyl group. The fluoroalkyl group is more preferably a fluoroalkyl group having 2 to 8 carbon atoms, for example, a trifluoroethyl group, a tetrafluoropropyl group, a hexafluoroisopropyl group, an octafluoropentyl group, and a dodecafluorooctyl group, most preferably a trifluoroethyl group.

As the polymerizable functional group of the component B, the same functional group as that of the component A can be used. From the viewpoint of the polymerization reaction, the polymerizable functional group of the component B is most preferably the same polymerizable functional group as that of the component A.

As the component B, a (meth)acrylic acid fluoroalkyl ester is most preferable because it has a significant effect of providing a skin adhesive sheet that is flexible and excellent in mechanical properties such as folding resistance. In particular, an acrylic acid fluoroalkyl ester is preferable. Specific examples of the (meth)acrylic acid fluoroalkyl ester include trifluoroethyl (meth)acrylate, tetrafluoroethyl (meth)acrylate, trifluoropropyl (meth)acrylate, tetrafluoropropyl (meth)acrylate, pentafluoropropyl (meth)acrylate, hexafluorobutyl (meth)acrylate, hexafluoroisopropyl (meth)acrylate, heptafluorobutyl (meth)acrylate, octafluoropentyl (meth)acrylate, nonafluoropentyl (meth)acrylate, dodecafluoropentyl (meth)acrylate, dodecafluoroheptyl (meth)acrylate, dodecafluorooctyl (meth)acrylate, and tridecafluoroheptyl (meth)acrylate. Preferably, the (meth)acrylic acid fluoroalkyl ester is trifluoroethyl (meth)acrylate, tetrafluoroethyl (meth)acrylate, hexafluoroisopropyl (meth)acrylate, octafluoropentyl (meth)acrylate, or dodecafluorooctyl (meth)acrylate. Most preferably, the (meth)acrylic acid fluoroalkyl ester is trifluoroethyl (meth)acrylate.

The copolymer of the present invention preferably contains 50 parts by mass or more of the components A and B in total based on 100 parts by mass in total of polymerization components. The copolymer preferably contains 20 to 90 parts by mass of the component B based on total polymerization components of the copolymer. From the viewpoint of achieving both the anti-fouling property and moderate flexibility, the content of the component B is more preferably 30 to 80 parts by mass, still more preferably 40 to 70 parts by mass, even more preferably 50 to 60 parts by mass.

The component B of the present invention may be used alone, or two or more kinds may be used in combination.

The component C is a polymerizable monomer having an alkyl group and having no fluoroalkyl group.

Since the alkyl group of the component C decreases cohesive energy, it has an effect of imparting rubber elasticity and flexibility to the copolymer. In addition, copolymerization of the component C greatly improves the surface adhesive strength of the copolymer, and makes the copolymer suitable for the skin adhesive sheet.

The component C is preferably a component that lowers the glass transition point of the copolymer to room temperature, or 0° C. or lower. As the polymerizable functional group of the component C, the same functional group as that of the component A can be used. Preferable functional groups for the component C are also the same as those for the component A. That is, the most preferable polymerizable monomer as the component C is a (meth)acrylic monomer. From the viewpoint of the polymerization reaction, the polymerizable functional group of the component C is most preferably the same polymerizable functional group as that of the component A.

The component C may have a plurality of polymerizable functional groups per molecule, but one having only one polymerizable functional group per molecule (monofunctional polymerizable monomer) is preferable. When the component C is a monofunctional polymerizable monomer, the crosslinking density decreases, the degree of freedom of the copolymer increases, and a moderately flexible skin adhesive sheet having low elastic modulus can be realized.

The upper limit of the number average molecular weight of the component C is preferably less than 1,000, more preferably less than 500, still more preferably less than 350. The lower limit is preferably 40 or more, more preferably 50 or more, still more preferably 80 or more.

Suitable specific examples of the alkyl group of the component C include alkyl groups having 1 to 20 carbon atoms, such as a methyl group, an ethyl group, a propyl group, an isopropyl group, a butyl group, a t-butyl group, a decyl group, a dodecyl group, and an octadecyl group. The alkyl group is more preferably an alkyl group having 2 to 8 carbon atoms, most preferably a hexyl group.

Suitable examples of the component C for improving the mechanical properties such as flexibility, folding resistance, and adhesive strength include (meth)acrylic acid alkyl esters, preferably (meth)acrylic acid alkyl esters having an alkyl group having 1 to 20 carbon atoms. Specific examples of the (meth)acrylic acid alkyl esters include methyl (meth)

acrylate, ethyl (meth)acrylate, n-propyl (meth)acrylate, n-butyl (meth)acrylate, tert-butyl (meth)acrylate, isobutyl (meth)acrylate, n-hexyl (meth)acrylate, n-octyl (meth)acrylate, 2-ethylhexyl (meth)acrylate, n-heptyl (meth)acrylate, n-nonyl (meth)acrylate, n-decyl (meth)acrylate, isodecyl (meth)acrylate, n-lauryl (meth)acrylate, tridecyl (meth)acrylate, n-dodecyl (meth)acrylate, cyclopentyl (meth)acrylate, cyclohexyl (meth)acrylate, and n-stearyl (meth)acrylate. More preferable examples of the (meth)acrylic acid alkyl esters include n-butyl (meth)acrylate, n-octyl (meth)acrylate, n-lauryl (meth)acrylate, and n-stearyl (meth)acrylate. Among these, a (meth)acrylic acid alkyl ester having an alkyl group having 1 to 10 carbon atoms is more preferable. Too large a number of carbon atoms of the alkyl group is not preferable because transparency of the obtained skin adhesive sheet may deteriorate.

The copolymer of the present invention preferably contains 1 to 18 parts by mass of the component C based on 100 parts by mass in total of polymerization components. If the content of the component C is less than 1 part by mass, the copolymer may be remarkably deteriorated in tackiness, or the compatibility among the polymerization components may be deteriorated so that the copolymer cannot be prepared. If the content of the component C is more than 18 parts by mass, the copolymer is brittle due to its small tensile elongation. Moreover, the skin adhesive sheet is remarkably increased in tackiness, and when being peeled off the skin, the skin adhesive sheet adheres to the skin too strongly so that the handling of the sheet is difficult, resulting in pain of the skin. The content of the component C is preferably 3 to 15 parts by mass, more preferably 5 to 12 parts by mass, most preferably 7 to 10 parts by mass from the viewpoint of achieving both the tackiness and moderate flexibility.

A preferable content of the component C is 100 parts by mass or less, more preferably 100 to 1 part by mass, still more preferably 60 to 1 part by mass, most preferably 30 to 1 part by mass, based on 100 parts by mass of the component A in the case of a copolymer not containing the component B, or based on 100 parts by mass in total of the two components A and B in the case of a copolymer containing the components A, B, and C as polymerization components. If the amount of the component C is too small, tackiness and flexibility are hardly obtained. If the amount of the component C is too large, white turbidity may occur, the mechanical properties such as folding resistance may be insufficient, or the skin adhesive sheet may be excessively increased in adhesive strength, resulting in pain of the skin when the sheet is peeled off the skin.

The component C may be used alone, or two or more kinds may be used in combination.

The copolymer of the present invention may further contain the component M as a polymerization component. The component M is a monomer having only one polymerizable functional group per molecule and having a siloxanyl group. When the copolymer contains the component M, the crosslinking density decreases, the degree of freedom of the copolymer increases, and a moderately flexible skin adhesive sheet having low elastic modulus can be realized.

The siloxanyl group of the component M is preferably linear. When the siloxanyl group is linear, the shape recovery properties of the obtained skin adhesive sheet are improved. As used herein, a linear structure refers to a structure represented by one linear Si—(O—Si)$_{n-1}$—O—Si bond (wherein n represents an integer of 2 or more) in which silicon atoms bonded to a group having a polymerizable group serve as a starting point.

The number average molecular weight of the component M is preferably 300 to 120,000. When the number average molecular weight of the component M is within the above-mentioned range, it is possible to obtain a flexible (low elastic modulus) base material that is excellent in mechanical properties such as folding resistance. If the number average molecular weight of the component M is small, mechanical properties such as folding resistance and shape recovery properties tend to deteriorate. Therefore, the number average molecular weight of the component M is more preferably 500 or more. If the number average molecular weight of the component M is too large, flexibility and transparency tend to deteriorate. The number average molecular weight of the component M is more preferably within the range of 1,000 to 25,000, still more preferably within the range of 5,000 to 15,000.

As the polymerizable functional group of the component M, the same functional group as that of the component A can be used. From the viewpoint of the polymerization reaction, the polymerizable functional group of the component M is most preferably the same polymerizable functional group as that of the component A.

The component M preferably has a structure of the following formula (ML1):

[Chemical Formula 3]

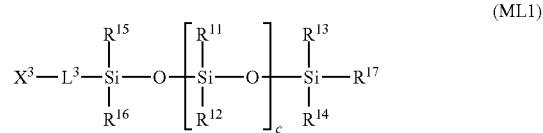

(ML1)

wherein $X^3$ represents a polymerizable functional group; $R^{11}$ to $R^{17}$ each independently represent a substituent selected from hydrogen, an alkyl group having 1 to 20 carbon atoms, a phenyl group, and a fluoroalkyl group having 1 to 20 carbon atoms; $L^3$ represents a divalent group; c is number of repetitions of siloxane units, and represents an integer of 1 to 700; and structures of the siloxane units may be the same or different.

$X^3$ is preferably a radical polymerizable functional group, and is preferably a radical polymerizable functional group having a carbon-carbon double bond. Examples of preferable polymerizable functional groups include a vinyl group, an allyl group, a (meth)acryloyl group, an α-alkoxymethylacryloyl group, a maleic acid residue, a fumaric acid residue, an itaconic acid residue, a crotonic acid residue, an isocrotonic acid residue, and a citraconic acid residue. Among these polymerizable functional groups, a (meth)acryloyl group is most preferable because it has high polymerizability. That is, the component M is most preferably a (meth)acrylic monomer having one (meth)acryloyl group.

Further, the polymerizable functional group of the component M is more preferably copolymerizable with the polymerizable functional group of the component A, since a skin adhesive sheet having satisfactory mechanical properties can be easily obtained. The polymerizable functional group of the component M is still more preferably the same as the polymerizable functional group of the component A, since a skin adhesive sheet having satisfactory surface properties can be easily obtained due to uniform copolymerization of the components M and A.

$R^{11}$ to $R^{17}$ each independently represent a substituent selected from hydrogen, an alkyl group having 1 to 20 carbon atoms, a phenyl group, and a fluoroalkyl group having 1 to 20 carbon atoms. Suitable specific examples of $R^{11}$ to $R^{19}$ include hydrogen; alkyl groups having 1 to 20 carbon atoms, such as a methyl group, an ethyl group, a propyl group, an isopropyl group, a butyl group, a t-butyl group, a decyl group, a dodecyl group, and an octadecyl group; a phenyl group; and fluoroalkyl groups having 1 to 20 carbon atoms, such as a trifluoromethyl group, a trifluoroethyl group, a trifluoropropyl group, a tetrafluoropropyl group, a hexafluoroisopropyl group, a pentafluorobutyl group, a heptafluoropentyl group, a nonafluorohexyl group, a hexafluorobutyl group, a heptafluorobutyl group, an octafluoropentyl group, a nonafluoropentyl group, a dodecafluoroheptyl group, a tridecafluoroheptyl group, a dodecafluorooctyl group, a tridecafluorooctyl group, a hexadecafluorodecyl group, a heptadecafluorodecyl group, a tetrafluoropropyl group, a pentafluoropropyl group, a tetradecafluorooctyl group, a pentadecafluorooctyl group, an octadecafluorodecyl group, and a nonadecafluorodecyl group. Among these groups, hydrogen and a methyl group are more preferable, and a methyl group is most preferable from the viewpoint of imparting satisfactory mechanical properties and high oxygen permeability to the skin adhesive sheet.

As $L^3$, a group same as $L^1$ or $L^2$ in the general formula (A1) can be preferably used.

In the formula (ML1), the number c of repetitions of siloxane units is preferably 3 or more, more preferably 10 or more, still more preferably 10 to 500, even more preferably 30 to 300, particularly preferably 50 to 200.

The content of the component M is preferably 5 to 200 parts by mass, more preferably 7 to 150 parts by mass, still more preferably 10 to 100 parts by mass based on 100 parts by mass of the component A. If the content of the component M is less than 5 parts by mass based on 100 parts by mass of the component A, the crosslinking density tends to increase and the sheet tends to be hard. If the content of the component M is more than 200 parts by mass based on 100 parts by mass of the component A, the sheet is soft and tends to be easily broken. If the content of the component M is small, the crosslinking density tends to increase and the sheet tends to be hard. Alternatively, if the content of the component M is large, the sheet is soft.

The component M may be used alone, or two or more kinds may be used in combination.

Furthermore, the copolymer in the skin adhesive sheet of the present invention may be obtained by further copolymerizing the following monomers in order to improve the mechanical properties, dimensional stability, and the like of the skin adhesive sheet.

Examples of the monomers for improving the mechanical properties include aromatic vinyl compounds such as styrene and styrene derivatives.

Examples of the monomers for improving the dimensional stability of the skin adhesive sheet include ethylene glycol dimethacrylate, diethylene glycol dimethacrylate, triethylene glycol dimethacrylate, polyethylene glycol dimethacrylate, trimethylolpropane trimethacrylate, pentaerythritol tetramethacrylate, bisphenol A dimethacrylate, vinyl methacrylate, acrylic methacrylate, acrylates corresponding to these methacrylates, divinylbenzene, and triallyl isocyanurate.

In addition, the silicon atom content in the skin adhesive sheet of the present invention in a dry state is preferably 5% by mass or more, more preferably 10% by mass or more, still more preferably 15% by mass or more. In addition, the sum of the silicon atom content and the fluorine atom content in the skin adhesive sheet of the present invention in a dry state is preferably 5% by mass or more, more preferably 10% by mass or more, still more preferably 15% by mass or more. If the silicon atom content or the fluorine atom content is small, white turbidity may occur in the skin adhesive sheet, or the mechanical properties such as folding resistance tend to be insufficient.

The silicon atom content based on the dry weight of the skin adhesive sheet can be measured by an inductively coupled plasma (ICP) emission spectrometer (suitably a sequential ICP emission spectrometer SPS4000 manufactured by Seiko Instruments Inc.). The measurement method is as follows.

First, the skin adhesive sheet is brought into a dry state. Herein, the dry state means a state after the skin adhesive sheet is vacuum-dried at 40° C. and at 2 hPa or less for 16 hours. The skin adhesive sheet (4 to 5 mg) in a dry state is weighed in a platinum crucible, sulfuric acid is added thereto, and then the skin adhesive sheet is incinerated by heating using a hot plate and a burner. The obtained calcareous material is melted with sodium carbonate, and water is added thereto. After dissolution by heating, nitric acid is added, and the volume of the solution is fixed with water. As for this solution, silicon atoms are measured by ICP emission spectrometry, and the silicon atom content in the skin adhesive sheet is determined. The fluorine atom content based on the dry weight of the skin adhesive sheet can also be determined in the same manner.

The copolymer of the present invention preferably has a crosslinking degree within the range of 2.0 to 18.3. The crosslinking degree is represented by the following equation (Q1).

[Equation 1]

$$\text{Crosslinking degree} = \frac{\sum_{n=1}^{\infty} \{Mn \times (n-1)\}}{\sum_{n=1}^{\infty} Wn} \quad (Q1)$$

In the equation (Q1), Mn represents the total molar number (mmol) of a monomer having n polymerizable groups per molecule, and Wn represents the total mass (kg) of the monomer having n polymerizable groups per molecule. When the molecular weight of the monomer has distribution, the molar number is calculated using the number average molecular weight.

If the crosslinking degree of the copolymer is less than 2.0, the copolymer may become difficult to handle because it is too soft. If the crosslinking degree of the copolymer is more than 18.3, the copolymer is too hard and tends to be deteriorated in usability. The crosslinking degree is more preferably within the range of 3.5 to 16.0, still more preferably within the range of 8.0 to 15.0, most preferably within the range of 9.0 to 14.0.

The skin adhesive sheet of the present invention preferably has a surface adhesive strength of 10 to 90 g/10 mm. If the adhesive strength is too small, the skin adhesive sheet applied to the skin surface is poor in adhesion to the skin and easily peeled off the skin. In particular, when the skin adhesive sheet is applied to a wound site, the skin surface may be vulnerable to airborne infection. On the other hand, if the adhesive strength is too large, when the skin adhesive sheet is peeled off the skin, the sheet adheres to the skin too strongly so that the handling of the sheet is difficult, resulting in pain of the skin. Therefore, the surface adhesive strength is more preferably 30 g/10 mm or more, still more preferably 50 g/10 mm or more. In addition, the surface adhesive strength is more preferably 80 g/10 mm or less. The adhesive strength in the present invention is a value measured in terms of 180° peel strength according to JIS Z 0237: adhesive tape/adhesive sheet test method.

The skin adhesive sheet of the present invention has a water content less than 10% by mass. When the water content is less than 10% by mass, the skin adhesive sheet is good in adhesion to the skin and suppressed in evaporation of the drug solution or the like, so that the sheet causes little feeling of dryness when applied to the skin. In addition, a low water content can also suppress the risk of bacteria growth. The water content of the skin adhesive sheet of the present invention is more preferably less than 5% by mass, still more preferably less than 2% by mass, most preferably less than 1% by mass. A copolymer having a water content less than 10% by mass can be obtained by appropriately adjusting and polymerizing the components A and C, and other components as necessary according to the disclosure of the present description.

Herein, the water content of the skin adhesive sheet is calculated from the mass in the dry state and the mass in the state of being wetted with pure water according to the formula {(mass in wet state)−(mass in dry state)}/(mass in wet state)×100.

The wet state means a state after the skin adhesive sheet is immersed in pure water at room temperature (25° C.) for 24 hours to be brought into an equilibrium state, and then the water on the surface is lightly wiped off. The dry state means a state after a specimen in a wet state is vacuum-dried at 40° C. and at 2 hPa or less for 16 hours.

The tensile elastic modulus of the skin adhesive sheet of the present invention is preferably 0.01 to 5 MPa, more preferably 0.1 to 3 MPa, still more preferably 0.1 to 2 MPa, even more preferably 0.1 to 1 MPa, most preferably 0.1 to 0.6 MPa. If the tensile elastic modulus is too small, the skin adhesive sheet is too soft and tends to be difficult to handle. If the tensile elastic modulus is too large, the skin adhesive sheet is too hard and tends to be deteriorated in usability. The tensile elastic modulus is a value measured by using a test piece in a dry state.

The tensile elongation of the skin adhesive sheet of the present invention is preferably 200% to 2000%, more preferably 640% to 1500%. If the tensile elongation is small, the adhesive sheet tends to be easily broken. If the tensile elongation is too large, the adhesive sheet tends to be easily deformed. The tensile elongation is a value measured by using a test piece in a dry state.

The skin adhesive sheet of the present invention preferably has an oxygen permeability [×10$^{-11}$ (cm$^2$/sec) mLO$_2$/(mL·hPa)] of 50 to 2,000, more preferably 100 to 1,500, still more preferably 200 to 1,000, even more preferably 300 to 700. However, if the oxygen permeability is excessively large, an adverse influence may be exerted on other physical properties such as mechanical properties. The oxygen permeability is a value measured by using a test piece in a dry state.

The ratio of shrinkage by drying (hereinafter referred to as the ratio of shrinkage) of the skin adhesive sheet of the present invention is preferably 20 or less, more preferably 10 or less, still more preferably 5 or less, even more preferably less than 1.

The ratio of shrinkage is determined by measuring the lengths of four sides of a test piece in a state of being wetted with pure water (before storage) and the lengths of four sides of the test piece after being stored in a predetermined environment for a predetermined time, and calculating the ratios of shrinkage of the four sides by the following equation. The ratio of shrinkage is evaluated by the average value of the four ratios of shrinkage.

Ratio of shrinkage (%) of one side={(length of one side before storage)−(length of one side after storage)}/(length of one side before storage)×100

The skin adhesive sheet of the present invention may further contain components such as an ultraviolet absorber, a pigment, a colorant, a slip agent, a pharmaceutical and a nutritional supplementary component, a compatibilizing component, an antibacterial component, and a mold release agent. When these components are used, the content of these components is preferably 100 parts by mass or less based on 100 parts by mass in total of the components A, B (when the component B is contained), and C since these components may cause turbidity of the adhesive sheet. When the skin adhesive sheet contains an ultraviolet absorber, it can protect the wearer's skin from harmful ultraviolet rays. When the skin adhesive sheet contains a colorant, the skin adhesive sheet is colored, resulting in easy identification and improvement in convenience during handling.

Any of the above-mentioned components may be contained in the copolymer as a polymerization component or as a non-polymerization component. The component is preferably contained as a polymerization component because the component is fixed and the possibility of elution is reduced.

The skin adhesive sheet of the present invention together with a drug solution held on the surface thereof can be used as a sheet-like external preparation for skin. Such a sheet-like external preparation for skin can allow a drug solution to percutaneously permeate or enter from a wound site while preventing the flowing out or evaporation of the drug solution from the skin.

Incidentally, the drug solution in the present invention encompasses not only those containing pharmaceutical and quasi-drug components, but also beauty essences such as lotions and emulsions intended for cosmetic effects, and cleansing agents. That is, the sheet-like external preparation for skin of the present invention can be suitably used as a fomentation, a wound dressing or the like for medical purposes, and a beauty pack, a face mask, a make-up remover or the like for cosmetic purposes. In particular, the aspect in which the sheet-like external preparation for skin holds a beauty essence is one of the most preferable aspects of the present invention.

Examples of components contained in the beauty essence held in the sheet-like external preparation for skin of the present invention include moisturizing ingredients such as saccharides, amino acids, placenta extract, hyaluronic acid, glycerin, sorbitol, and polyethylene glycol, softeners such as olive oil, cetyl alcohol, lanolin, and stearyl alcohol, blood circulation accelerating agents such as vitamin E, anti-inflammatory agents such as glycyrrhizic acid, and whitening components such as various vitamin C's.

Examples of the cleansing agent include ethanol, isopropanol, propylene glycol, glycerin, polyethylene glycol, cyclic silicone, liquid paraffin, and POE. In addition, the cleansing agent may also contain a moisturizer, a whitening component, vitamins and the like.

Examples of applicable techniques of making the surface of the skin adhesive sheet hold the drug solution include various techniques such as an immersion method, a brush coating method, a spray coating method, a spin coating method, a die coating method, and a squeegee method. The amount of the drug solution used and the time for imparting the drug solution in each of these techniques are appropriately adjusted depending on the intended use.

The skin adhesive sheet of the present invention is preferably not coated with a hydrophilic substance. A skin adhesive sheet that does not have any coating of a hydrophilic substance has good adhesion to the skin surface and does not easily fall off the skin surface. Herein, the hydrophilic substance means a substance having an action of improving the wettability of the skin adhesive sheet surface, such as an acidic polymer, a basic polymer, and a naturally derived polymer.

As an example of a method for producing the skin adhesive sheet of the present invention, a method of polymerizing a raw material composition containing the components A, B, and C by a mold polymerization method will be described.

First, a gap between two mold members each having a fixed shape is filled with the raw material composition. Examples of the material of the mold member include resin, glass, ceramics, and metal. In the case where photopolymerization is performed, transparent resin or glass is preferably used since an optically transparent material is preferable. Depending on the shape of the mold member or properties of the raw material composition, a gasket may be used so as to impart a fixed thickness to the skin adhesive sheet, and to prevent liquid leakage of the raw material composition filled in the gap.

The molds holding the raw material composition in the gap are subsequently irradiated with active rays such as ultraviolet rays, visible rays, or a combination thereof, or heated in an oven or a liquid bath. That is, the raw material composition filled into the gap is polymerized by photopolymerization through irradiation with active rays or thermal polymerization through heating. Alternatively, the two polymerization methods may be used in combination: e.g. photopolymerization and the subsequent thermal polymerization, or thermal polymerization and the subsequent photopolymerization. Examples of a specific aspect of photopolymerization include a method of applying light including ultraviolet rays, such as light of a mercury lamp or an ultraviolet lamp (for example, FL15BL, TOSHIBA CORPORATION) for a short time (usually 1 hour or less). In the case where thermal polymerization is performed, a method of gradually heating the composition from about room temperature, and raising the temperature to 60° C. to 200° C. over several to several tens of hours is preferable so as to maintain optical uniformity and quality of the skin adhesive sheet, and to enhance reproducibility.

In the polymerization, a polymerization initiator such as a thermal polymerization initiator typified by a peroxide or an azo compound, or a photopolymerization initiator is preferably added so as to facilitate the polymerization. In the case where thermal polymerization is performed, an initiator having optimum decomposition characteristics at a desired reaction temperature is selected. In general, an azo-based initiator and a peroxide-based initiator, each having a ten-hour half-life temperature of 40 to 120° C., are suitable. Examples of the photoinitiator in the case where photopolymerization is performed include a carbonyl compound, a peroxide, an azo compound, a sulfur compound, a halogen compound, and a metal salt. These polymerization initiators are used alone or in combination. The amount of the polymerization initiator is preferably 5% by mass or less based on the polymerization components in total.

At the time of polymerization, a polymerization solvent can be used. Various organic and inorganic polymerization solvents can be used. Examples of the polymerization solvent include water; alcohol-based solvents such as methyl alcohol, ethyl alcohol, normal propyl alcohol, isopropyl alcohol, normal butyl alcohol, isobutyl alcohol, t-butyl alcohol, t-amyl alcohol, tetrahydrolinalool, ethylene glycol, diethylene glycol, triethylene glycol, tetraethylene glycol, and polyethylene glycol; glycol ether-based solvents such as methyl cellosolve, ethyl cellosolve, isopropyl cellosolve, butyl cellosolve, propylene glycol monomethyl ether, diethylene glycol monomethyl ether, triethylene glycol monomethyl ether, polyethylene glycol monomethyl ether, ethylene glycol dimethyl ether, diethylene glycol dimethyl ether, triethylene glycol dimethyl ether, and polyethylene glycol dimethyl ether; ester-based solvents such as ethyl acetate, butyl acetate, amyl acetate, ethyl lactate, and methyl benzoate; aliphatic hydrocarbon-based solvents such as normal hexane, normal heptane, and normal octane; alicyclic hydrocarbon-based solvents such as cyclohexane and ethylcyclohexane; ketone-based solvents such as acetone, methyl ethyl ketone, and methyl isobutyl ketone; aromatic hydrocarbon-based solvents such as benzene, toluene, and xylene; and petroleum-based solvents. These polymerization solvents may be used alone, or two or more kinds may be used in combination.

EXAMPLES

The present invention will be specifically described below by way of examples, but the present invention is not limited thereto.

Measurement methods of various physical properties are as follows.

<Contents of Silicon Atoms and Fluorine Atoms>

A skin adhesive sheet (4 to 5 mg) in a dry state was weighed in a platinum crucible, sulfuric acid was added thereto, and then the skin adhesive sheet was incinerated by heating using a hot plate and a burner. The obtained calcareous material was melted with sodium carbonate, and water was added thereto. After dissolution by heating, nitric acid was added, and the volume of the solution was fixed with water. As for this solution, the contents of silicon atoms and fluorine atoms in the skin adhesive sheet were measured by ICP emission spectrometry using a sequential ICP emission spectrometer (SPS4000 manufactured by Seiko Instruments Inc.).

<Water Content>

A test piece of the skin adhesive sheet was immersed in three beakers containing clean water (200 mL each) each for 2 seconds without any time interval, and then washed. Then, the test piece was immersed in water containing clean water (200 mL) and allowed to stand at room temperature for 24 hours. Then, water on the surface of the test piece was wiped off with a wiping cloth ("Kimwipe (registered trademark)" manufactured by NIPPON PAPER CRECIA CO., LTD.), and the mass of the test piece in a wet state (W1) was measured. Then, the test piece was dried in a vacuum drying oven at 40° C. for 16 hours, and the mass of the test piece in a dry state (W2) was measured. The water content was determined by the following equation. If the obtained value was less than 1%, the water content was judged as unmeasurable, and was recorded as "0%".

$$\text{Water content (\%)} = (W1 - W2)/W1 \times 100$$

<Tensile Elastic Modulus and Tensile Elongation>

Using a prescribed blanking die, test pieces each 5 mm in width (narrowest portion) and 14 mm in length were cut from a sample of the skin adhesive sheet. The test pieces were subjected to a tensile test using TENSILON model RTM-100 manufactured by ORIENTEC CORPORATION. The tension rate was 100 mm/min, and the distance between grips (initial) was 5 mm. The number N of test pieces was 8. The average value of the values excluding the maximum value and the minimum value was taken as the value of tensile elastic modulus or tensile elongation.

<Static Contact Angle>

An automatic contact angle meter CONTACT-ANGLE METER (model CA-D, manufactured by Kyowa Interface Science Co., Ltd.) was used. In preparation for the sample, nitrogen was sprayed to the center of a 3-cm square film sample for about 5 seconds, and the surface was dried. Then, droplets of about 1 µL of RO water were applied, and the contact angle at that time was measured. The number N of samples was 3. The average value was taken as the static contact angle.

<Adhesive Strength>

The adhesive strength of the skin adhesive sheet obtained in each of the examples and comparative examples was evaluated in terms of 180° peel strength according to JIS Z 0237: adhesive tape/adhesive sheet test method. As a sample, the obtained skin adhesive sheet was allowed to stand at normal temperature (23° C.) and a humidity of 50% overnight. Then, the sample was cut into a width of 10 mm, polished with No. 360 water-proof abrasive paper prescribed in JIS G 4305, and then adhered to an alcohol-washed stainless steel piece (SUS 304, 2 mm in thickness×about 50 mm in width×about 125 mm in length). The sample was pressure-bonded to the stainless steel piece by moving a 2 kg roller back and forth twice. After 20 to 40 minutes of the bonding, the sample was set in an AUTOGRAPH machine. The 180° peel strength was measured at a tension rate of 300 mm/min. The measurement was performed three times, and the average value was taken as the adhesive strength.

<Evaluation of Adhesive Strength to Skin>

A 6-cm square skin adhesive sheet obtained in each of the examples and comparative examples was applied to the back of a human hand. Immediately after that, the period during which the entire surface of the skin adhesive sheet was adhered to the back of the hand was measured in a state where the back of the hand was inclined 180°. The adhesive strength of the skin adhesive sheet to the skin was evaluated based on the following five-point scale A to E.
A: 60 minutes or more
B: within 30 to 60 minutes
C: within 5 to 30 minutes
D: within 1 second to 5 minutes
E: 1 second or less <Drug Solution Holding Power>

A 6-cm square sheet obtained in each of the examples and comparative examples was immersed in the drug solution shown in each of the examples and comparative examples for about 5 seconds, and then withdrawn from the drug solution with two ends at the top of the sheet being held with two ring tweezers. Immediately after that, the period required for the drug solution on the sheet surface to flow down by half of the length of the sheet longitudinal axis from the top of the sheet fixed with the ring tweezers to the bottom of the sheet was visually confirmed, and the period was measured with a stopwatch. The drug solution holding power was evaluated based on the following three-point scale A to C.
A: 5 seconds or more
B: 2 seconds or more and less than 5 seconds
C: less than 2 seconds <Evaluation of Residual Drug Solution>

After being immersed in the drug solution shown in each of the examples and comparative examples for about 5 seconds, the skin adhesive sheet was withdrawn from the drug solution. Immediately after that, the skin adhesive sheet was applied to the skin surface for 6 hours. The surface of the skin after the skin adhesive sheet was peeled off was observed, and the residual drug solution was evaluated according to the following criteria based on the approximate percentage of the visually recognized drug solution remaining on the skin surface on which the skin adhesive sheet (sheet-like external preparation for skin) had been present.
A: about 75 to 100%
B: about 50 to 75%
C: about 25 to 50%
D: about 10 to 25%
E: less than 10%

<Ratio of Shrinkage>

The sheet prepared in each of the examples and comparative examples was made to hold a drug solution, and was applied to the skin surface at room temperature (23° C.) for 6 hours. After that, the average value of the ratios of shrinkage of the sides was taken as the ratio of shrinkage of the skin adhesive sheet.

Example 1

To polydimethylsiloxane (FM7726, JNC Corporation, Mw: 30,000) having a methacryloyl group at both ends (35 parts by mass) as the component A, trifluoroethyl acrylate (Viscoat (registered trademark) 3F, OSAKA ORGANIC CHEMICAL INDUSTRY LTD.) (58 parts by mass) as the component B, and 2-ethylhexyl acrylate (Tokyo Chemical Industry Co., Ltd.) (7 parts by mass) as the component C, IRGACURE (registered trademark) 819, NAGASE & CO., LTD. (5000 ppm) and tert-amyl alcohol (10 parts by mass) were mixed and stirred to give a uniform and transparent monomer mixture. Between two 10-cm square glass plates each having a thickness of 3 mm, the center of two parafilms each having a thickness of 100 µm was sandwiched as spacers. The gap formed by the glass plates and the spacers was filled with the monomer mixture, and the mixture was cured by irradiation with light (wavelength: 405 nm (±5 nm), illuminance: 0 to 0.7 mW/cm², 30 minutes) to give a sheet made from a copolymer. The obtained sheet was immersed in a 100% by mass aqueous solution of isopropanol (IPA) at 60° C. for 2 hours to extract impurities such as residual monomers. Then, the sheet was dried at room temperature (23° C.) for 12 hours.

The obtained skin adhesive sheet was transparent, and had a silicon atom content and a fluorine atom content based on the dry weight of the sheet of 13.2% and 19.7%, respectively, a water content of 0%, a tensile elastic modulus of 0.48 MPa, a tensile elongation of 978%, a static contact angle of 84°, and an adhesive strength evaluation of 50 g/10 mm. The evaluation of adhesive strength to skin was A.

The obtained skin adhesive sheet was immersed in a glycerin stock solution for about 5 seconds to give a sheet-like external preparation for skin including glycerin held on the surface thereof. The evaluation of drug solution holding power was A. The evaluation of residual drug solution after the sheet was applied to the skin surface for 6 hours was A. In addition, the ratio of shrinkage after the sheet was applied to the skin surface for 6 hours was 0%, and the sheet was suitable as a skin adhesive sheet.

In addition, the skin adhesive sheet was immersed in a lotion ("AQUA LABEL" (registered trademark), Shiseido Co., Ltd.) for about 5 seconds to give a sheet-like external preparation for skin including the lotion held on the surface thereof. The evaluation of drug solution holding power was A, and the evaluation of residual drug solution was also A. In addition, the ratio of shrinkage was 0%, and the sheet was suitable as a skin adhesive sheet.

Examples 2 to 10 and Comparative Examples 1 to 3

A sheet was prepared in the same manner as in Example 1 except that the contents of the components A, B, and C were changed as shown in Table 1.

Comparative Example 4

An attempt was made to prepare a monomer mixture in the same manner as in Example 1 except that polydimethylsiloxane (FM7726, JNC Corporation, Mw: 30,000) having a methacryloyl group at both ends (42 parts by mass) as the component A and trifluoroethyl acrylate (Viscoat 3F, OSAKA ORGANIC CHEMICAL INDUSTRY LTD.) (58 parts by mass) as the component B were used, and no component C was added. As a result, the components were separated, and a uniform monomer mixture was not obtained.

Comparative Example 5

Light irradiation was carried out in the same manner as in Example 1 except that no component A was added, and trifluoroethyl acrylate (Viscoat 3F, OSAKA ORGANIC CHEMICAL INDUSTRY LTD.) (93 parts by mass) as the component B was added. As a result, the components did not cure and no sheet was obtained.

Comparative Example 6

Light irradiation was carried out in the same manner as in Example 1 except that no components A and C were added, and trifluoroethyl acrylate (Viscoat 3F, OSAKA ORGANIC CHEMICAL INDUSTRY LTD.) (100 parts by mass) as the component B was added in Example 1. As a result, the components did not cure and no sheet was obtained.

Comparative Example 7

An attempt was made to prepare a monomer mixture in the same manner as in Example 1 except that polydimethylsiloxane (FM7726, JNC Corporation, Mw: 30,000) having a methacryloyl group at both ends (5 parts by mass) as the component A and trifluoroethyl acrylate (Viscoat 3F, OSAKA ORGANIC CHEMICAL INDUSTRY LTD.) (5 parts by mass) as the component B were used, and 2-phenoxyethyl acrylate (Tokyo Chemical Industry Co., Ltd.) (90 parts by mass) was used instead of the component C. As a result, the components were separated, and a uniform monomer mixture was not obtained.

Comparative Example 8

An attempt was made to prepare a monomer mixture in the same manner as in Comparative Example 7 except that the contents of the components A and B, and 2-phenoxyethyl acrylate were changed as shown in Table 1. As a result, the components were separated, and a uniform monomer mixture was not obtained.

Table 1 summarizes the water content, static contact angle, adhesive strength, and evaluation results of adhesive strength to the skin, drug solution holding power, and residual drug solution for the examples and comparative examples.

Reference Example 1

A commercially available silicone film ("Ultrathin SR Sheet", AS ONE Corporation) having a thickness of 0.2 mm had a water content of 0%, a tensile elastic modulus of 0.83 MPa, a tensile elongation of 1298%, a static contact angle of 95°, and an adhesive strength evaluation of 0 g/10 mm. The evaluation of adhesive strength to skin was B, and the film was poor in adhesive strength. Slight white turbidity was visually observed.

The commercially available silicone film was immersed in a glycerin stock solution for about 5 seconds. The evaluation of drug solution holding power was C. In addition, the evaluation of residual drug solution after the film was applied to the skin surface for 6 hours was C.

Similarly, the commercially available silicone film was immersed in a lotion ("AQUA LABEL", Shiseido Co., Ltd.) for about 5 seconds. The evaluation of drug solution holding power was C, and the evaluation of residual drug solution was also C.

TABLE 1

| | Component A (FM7726) | Component B (Trifluoroethyl acrylate) | Component C (2-Ethylhexyl acrylate) | Other polymerization components (2-Phenoxyethyl acrylate) | Silicon atom content (%) | Fluorine atom content (%) | Adhesive strength (g/10 mm) | Water content (%) |
|---|---|---|---|---|---|---|---|---|
| | | Content (parts by mass) based on total polymerization components | | | | | | |
| Example 1 | 35 | 58 | 7 | — | 13.2 | 19.7 | 50 | 0 |
| Example 2 | 35 | 50 | 15 | — | 13.2 | 17 | 30 | 0 |
| Example 3 | 35 | 47 | 18 | — | 13.2 | 15.6 | 30 | 0 |
| Example 4 | 35 | 62 | 3 | — | 13.2 | 21.1 | 20 | 0 |
| Example 5 | 99 | 0 | 1 | — | 37.3 | 0 | 10 | 0 |
| Example 6 | 97 | 0 | 3 | — | 36.6 | 0 | 10 | 0 |
| Example 7 | 82 | 0 | 18 | — | 30.9 | 0 | 30 | 0 |
| Example 8 | 80 | 0 | 20 | — | 30.1 | 0 | 30 | 0 |
| Example 9 | 60 | 0 | 40 | — | 22.6 | 0 | 30 | 0 |
| Example 10 | 50 | 0 | 50 | — | 18.8 | 0 | 99 | 0 |
| Comparative Example 1 | 80 | 20 | 0 | — | 30.1 | 6.8 | 0 | 0 |
| Comparative Example 2 | 51 | 49 | 0 | — | 19.2 | 16.6 | 0 | 0 |

TABLE 1-continued

| | | | | | | | | |
|---|---|---|---|---|---|---|---|---|
| Comparative Example 3 | 100 | 0 | 0 | — | 37.6 | 0 | 0 | 0 |
| Comparative Example 4 | 42 | 58 | 0 | — | — | — | — | — |
| Comparative Example 5 | 0 | 93 | 7 | — | — | — | — | — |
| Comparative Example 6 | 0 | 100 | 0 | — | — | — | — | — |
| Comparative Example 7 | 5 | 5 | 0 | 90 | — | — | — | — |
| Comparative Example 8 | 35 | 14 | 0 | 51 | — | — | — | — |

| | Tensile elastic modulus (MPa) | Tensile elongation (%) | Static contact angle (°) | Ratio of shrinkage (%) | Adhesive strength to skin (A to E) | Drug solution | Drug solution holding power (A to C) | Residual drug solution (A to E) |
|---|---|---|---|---|---|---|---|---|
| Example 1 | 0.48 | 978 | 84 | 0 | A | Glycerin | A | A |
| | | | | | | Lotion | A | A |
| Example 2 | 0.43 | 743 | 115 | 0 | A | Glycerin | A | A |
| Example 3 | 0.33 | 818 | 114 | 0 | A | Glycerin | A | A |
| Example 4 | 0.53 | 881 | 115 | 0 | A | Glycerin | A | A |
| Example 5 | 0.47 | 665 | 119 | 0 | A | Glycerin | A | A |
| Example 6 | 0.57 | 644 | 118 | 0 | A | Glycerin | A | A |
| Example 7 | 0.5 | 658 | 114 | 0 | A | Glycerin | A | A |
| Example 8 | 0.5 | 620 | 96 | 0 | A | Glycerin | A | A |
| Example 9 | 0.28 | 560 | 100 | 0 | A | Glycerin | A | A |
| Example 10 | 0.6 | 1020 | 110 | 0 | A | Glycerin | A | A |
| Comparative Example 1 | 0.7 | 1009 | 115 | 0 | D | — | — | — |
| Comparative Example 2 | 0.56 | 1050 | 111 | 0 | D | — | — | — |
| Comparative Example 3 | 0.8 | 1159 | 114 | 0 | D | Glycerin | C | C |
| | | | | | | Lotion | C | C |
| Comparative Example 4 | — | — | — | — | — | — | — | — |
| Comparative Example 5 | — | — | — | — | — | — | — | — |
| Comparative Example 6 | — | — | — | — | — | — | — | — |
| Comparative Example 7 | — | — | — | — | — | — | — | — |
| Comparative Example 8 | — | — | — | — | — | — | — | — |

The invention claimed is:

1. A skin adhesive sheet, comprising a copolymer containing the following components A and C as polymerization components, and having a water content less than 10% by mass, and comprising 7 to 40 parts by mass of the component C based on 100 parts by mass in total of polymerization components of the copolymer:
   component A: a polysiloxane macromonomer having a plurality of polymerizable functional groups per molecule, and having a number average molecular weight of 6,000 or more; and
   component C: a polymerizable monomer having an alkyl group and having no fluoroalkyl group, wherein component C is a (meth)acrylic acid alkyl ester,
   wherein the skin adhesive sheet is not coated with a hydrophilic substance.

2. The skin adhesive sheet according to claim 1, wherein the copolymer contains 50 parts by mass or more of the component A based on total polymerization components.

3. The skin adhesive sheet according to claim 1, wherein the copolymer further contains the following component B as a polymerization component:
   component B: a polymerizable monomer having a fluoroalkyl group.

4. The skin adhesive sheet according to claim 3, wherein the component B is a (meth)acrylic acid fluoroalkyl ester.

5. The skin adhesive sheet according to claim 3, wherein the copolymer contains 50 parts by mass or more of the components A and B in total based on total polymerization components.

6. The skin adhesive sheet according to claim 1, wherein the component A is a polysiloxane macromonomer represented by the following general formula (A1):

[Chemical Formula 1]

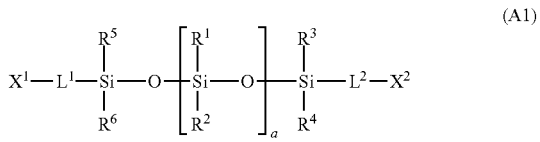

wherein $X^1$ and $X^2$ each independently represent a polymerizable functional group; $R^1$ to $R^6$ each independently represent a substituent selected from hydrogen, an alkyl group having 1 to 20 carbon atoms, a phenyl group, and a fluoroalkyl group having 1 to 20 carbon atoms; $L^1$ and $L^2$ each independently represent a divalent group; a is number of repetitions of siloxane units, and represents an integer of 1 to 1500; and structures of the siloxane units may be the same or different.

7. The skin adhesive sheet according to claim 1, wherein the copolymer further contains the following component M as a polymerization component:

component M: a monomer having one polymerizable functional group per molecule and having a siloxanyl group.

8. The skin adhesive sheet according to claim 1, wherein the copolymer has a crosslinking degree of 2.0 to 18.3.

9. The skin adhesive sheet according to claim 1, having a surface adhesive strength of 10 to 90 g/10 mm.

10. A sheet-like external preparation for skin, comprising the skin adhesive sheet according to claim 1, and a drug solution held on a surface of the skin adhesive sheet.

11. The sheet-like external preparation for skin according to claim 10, wherein the drug solution is a beauty essence.

\* \* \* \* \*